(12) United States Patent
Geddes et al.

(10) Patent No.: US 6,801,798 B2
(45) Date of Patent: Oct. 5, 2004

(54) BODY-MEMBER-ILLUMINATING PRESSURE CUFF FOR USE IN OPTICAL NONINVASIVE MEASUREMENT OF BLOOD PARAMETERS

(75) Inventors: Leslie A. Geddes, West Lafayette, IN (US); Kirk S. Foster, West Lafayette, IN (US); William E. Schoenlein, Lafayette, IN (US); Rebecca A. Roeder, Lafayette, IN (US); Claude B. Harrington, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 80 days.

(21) Appl. No.: 10/176,186

(22) Filed: Jun. 20, 2002

(65) Prior Publication Data

US 2003/0036690 A1 Feb. 20, 2003

Related U.S. Application Data

(60) Provisional application No. 60/299,462, filed on Jun. 20, 2001.

(51) Int. Cl.$^7$ .............................. A61B 5/00; A61B 5/02
(52) U.S. Cl. ....................... 600/323; 600/324; 600/344; 600/483; 600/499
(58) Field of Search ................................ 600/324, 344, 600/483, 485, 499, 502, 529, 310, 322, 323, 340

(56) References Cited

U.S. PATENT DOCUMENTS

| | | | |
|---|---|---|---|
| 4,202,347 A | * | 5/1980 | Sacks .......................... 600/490 |
| 4,543,962 A | | 10/1985 | Medero et al. |
| 4,638,810 A | | 1/1987 | Ramsey et al. |
| 4,685,464 A | | 8/1987 | Goldberger et al. |
| 4,830,014 A | | 5/1989 | Goodman et al. |
| 4,860,759 A | | 8/1989 | Kahn et al. |
| 4,869,261 A | | 9/1989 | Peñáz |
| 5,052,397 A | | 10/1991 | Ramsey et al. |
| 5,111,817 A | | 5/1992 | Clark et al. |
| 5,170,795 A | | 12/1992 | Ramsey et al. |
| 5,273,036 A | * | 12/1993 | Kronberg et al. ........... 600/529 |
| 5,505,207 A | | 4/1996 | Abbs et al. |
| 5,529,755 A | * | 6/1996 | Higashio et al. ............ 600/316 |
| 5,606,977 A | | 3/1997 | Ramsey et al. |
| 5,676,139 A | | 10/1997 | Goldberger et al. |
| 5,776,071 A | | 7/1998 | Inukai et al. |
| 5,827,181 A | * | 10/1998 | Dias et al. ................... 600/322 |
| 5,891,021 A | | 4/1999 | Dillon et al. |
| 6,106,478 A | | 8/2000 | Tochikubo et al. |
| 6,149,588 A | | 11/2000 | Noda et al. |
| 6,213,952 B1 | | 4/2001 | Finarov et al. |

OTHER PUBLICATIONS

John W. Severinghaus, M.D. and Yoshiyuki Honda, M.D., "History of Blood Gas Analysis. VII. Oximetry," *Journal of Clinical Monitoring*, Apr. 1987, pp. 135–138, vol. 3, No. 2.

L.A. Geddes, "Heritage of the Tissue–Bed Oximeter," *IEEE Engineering in Medicine and Biology*, Mar./Apr. 1997, pp. 87–91.

Ken–Ichi Yamakoshi, Hideaki Shimazu and Tatsuo Togawa, "Indirect Measurement of Instantaneous Arterial Blood Pressure in the Human Finger by the Vascular Unloading Technique," *IEEE Transactions on Biomedical Engineering*, Mar. 1980, pp. 150–155, vol. BME–27, No. 3.

Sokwoo Rhee, Boo–Ho Yang and Haruhiko Harry Asada, "Artifact–Resistant Power–Efficent Design of Finger–Ring Plethysmographic Sensors," *IEEE Transactions on Biomedical Engineering*, Jul. 2001, pp. 795–805, vol. 48, No. 7.

(List continued on next page.)

*Primary Examiner*—Eric F. Winakur
(74) *Attorney, Agent, or Firm*—William F. Bahret (57) ABSTRACT

A member-illuminating cuff for measurement of systolic, mean and diastolic pressure, oxygen saturation, pulse and respiratory rate in small body members, comprising a hinged cuff housing, one or more light sources mounted on a first section of the housing, a photodetector mounted on a second section of the housing, and a disposable, inflatable cuff adapted to fit within the cuff housing and around a body member placed therein.

23 Claims, 6 Drawing Sheets

OTHER PUBLICATIONS

Earl H. Wood, M.D., Ph.D., Julian R. B. Knutson, M.D. and Bowen E. Taylor, M.D., "Measurement of Blood Content and Arterial Pressure in the Human Ear," *Staff Meetings of the Mayo Clinic*, Jul. 5, 1950, pp. 398–405.

L. A. Geddes, M. Voelz, C. Combs, D. Reiner and C. F. Babbs, "Characterization of the Oscillometric Method for Measuring Indirect Blood Pressure," *Annals of Biomedical Engineering—The Journal of the Biomedical Engineering Society*, 1982, pp. 271–280, vol. 10, Pergamon Press Ltd., United States.

Maynard Ramsey III, "Noninvasive Automatic Determination of Mean Arterial Pressure," *Medical & Biological Engineering & Computing—Journal of the International Federation for Medical & Biological Engineering*, Jan. 1979, pp. 11–18, vol. 17, No. 1.

Patrick G. Yong, Bsee, and Leslie A. Geddes, ME, PhD, FACC, "The Effect of Cuff Pressure Deflation Rate on Accuracy in Indirect Measurement of Blood Pressure With the Auscultatory Method," *Journal of Clinical Monitoring*, Jul. 1987, pp. 155–159, vol. 3, No. 3.

L. A. Geddes, M.E., Ph.D., *The Direct and Indirect Measurement of Blood Pressure*, 1970, Year Book Medical Publishers, Inc., Chicago, Illinois, United States, pp. 70–98, 135–145.

L. A. Geddes, ME, PhD, *Handbook of Blood Pressure Measurement*, 1991, The Humana Press, Inc., Clifton, New Jersey, United States, pp. 88–107.

Posey et al., "The Meaning of the Point of Maximum Oscillations in Cuff Pressure in the Direct Measurement of Blood Pressure," Part 1, *Cardiovascular Research Center Bulletin.*, 1969, pp. 15–25, vol. 8, No. 1.

* cited by examiner

BODY-MEMBER-ILLUMINATING PRESSURE CUFF FOR USE IN OPTICAL NONINVASIVE MEASUREMENT OF BLOOD PARAMETERS

CROSS-REFERENCE TO RELATED APPLICATION

This application claims the benefit of U.S. Provisional Patent Application Ser. No. 60/299,462, filed Jun. 20, 2001, which provisional application is hereby incorporated by reference.

BACKGROUND OF THE INVENTION

This invention relates to the noninvasive measurement of parameters such as blood pressure and oxygen saturation in man and animals, and more particularly to the optical noninvasive measurement of blood parameters with a body-member-illuminating inflatable cuff.

A number of noninvasive methods of measuring blood parameters are known. For example, blood pressure has been measured by the auscultatory method which uses a cuff and a stethoscope, and by the oscillometric method which only requires a cuff applied to a body member. The conventional oscillometric method relies on the small-amplitude pulsatile pressure oscillations communicated to the cuff by the underlying artery in the body member during cuff deflation from above systolic pressure to zero pressure. Such arterial pressure oscillations cause corresponding oscillations in cuff pressure which can be amplified and used to identify systolic, mean and diastolic pressure. For example, it has been established by Posey et al. that the cuff pressure for maximal amplitude oscillations corresponds to mean arterial pressure. See Posey et al., "The Meaning of the Point of Maximum Oscillations in Cuff Pressure in the Direct Measurement of Blood Pressure," Part 1, *Cardiovascular Res. Ctr. Bull.* 8(1):15–25, 1969. See also Ramsey, "Noninvasive Automatic Determination of Mean Arterial Pressure," *Med. Biol. Eng. Comput.* 17:17–18, 1979; and Geddes et al., "Characterization of the Oscillometric Method for Measuring Indirect Blood Pressure," *Annals of Biomedical Engineering*, Vol. 10, pp. 271–280, 1982. All such references are incorporated herein by reference.

Commercially available oscillometric devices are useful for some applications but are not particularly suited for use in neonatology and premature infants, for example, where very small amplitude pressure pulses are encountered in such small limbs, and in small animal veterinary medicine where animal limbs and tails, etc. are too small for conventional oscillometric devices.

The pulse oximeter is a known instrument for noninvasive measurement of oxygen saturation, as described in a review article by Geddes entitled "Heritage of the Tissue-Bed Oximeter," published in *IEEE Engineering in Medicine and Biology*, 87–91, March/April 1997, said article being hereby incorporated by reference. However, conventional pulse oximeters do not include integral means for measuring blood pressure with the same sensors used for oximetry.

SUMMARY OF THE INVENTION

According to one aspect of the present invention, a transilluminating pressurizable cuff includes a hinged cuff housing having first and second semicylindrical sections and a hinge parallel to the longitudinal axis of the semicylindrical housing sections. One or more light sources are mounted on the first housing section, and a photodetector is mounted on the second housing section in a position to receive light transmitted from the light source(s) through a body member placed within the cuff housing. An optically transparent inflatable cuff is adapted to fit within the cuff housing and around the body member. The use of two circumferentially spaced light sources is preferred in order to minimize obstruction of the radiation beams by the bone.

One embodiment of the present invention provides an easily applied cuff for measurement of blood pressure and oxygen saturation in small body members, e.g., the limbs and tails of small animals and the limbs of infants, especially low birth-weight infants (below 8½ pounds).

Another aspect of the invention is an optical oscillometric method which is useful for small body members. The conventional oscillometric method relies on small-amplitude oscillations, or pulses, in cuff pressure. Successful application of the conventional method requires the presence of detectable pressure pulses in the cuff. Such pulses are extremely small in small children, and even smaller in neonates and premature infants. In these subjects the conventional oscillometric method is unreliable, and it is also unreliable in small animals. Instead of detecting cuff pressure pulses, the oscillometric method according to the present invention detects optical pulses, such as from a photodetector optically linked to a light source in a pressurizable cuff. The new method allows reliable, efficient detection of pulses useful for obtaining systolic, mean and diastolic pressure in small body members. In fact, it has been found that, the smaller the member, the larger the optical pulsatile signal.

DETAILED DESCRIPTION OF THE PREFERRED EMBODIMENT

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one of ordinary skill in the art to which the invention relates.

Figure 1:
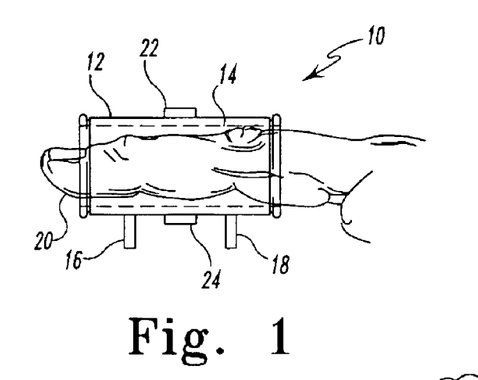
FIG. 1 is a side view of a cylindrical embodiment of a transilluminating cuff according to the present invention.

In one embodiment of a member-transilluminating, transparent pressurizable cuff 10 according to the present invention, illustrated in FIG. 1, a rigid tube 12 contains an elastic sleeve 14. The sleeve may be provided with an inlet 16 for connection to a pressure source, e.g., an air supply, and an outlet 18 for connection to, e.g., a manometer. Alternatively, inlet 16 may be the only pressure line, as in the embodiment of FIG. 2 described below. Pressure applied between the elastic sleeve and the rigid tube causes the sleeve to compress a body member therein such as a finger 20 placed therein. This embodiment is also useful on a small animal tail, for example, among other applications. The rigid tube includes a light source 22 and a photodetector 24 which may be diametrically opposed as illustrated in the drawing. Alternatively, two light sources may be provided as described below. In another alternative embodiment, the light source and photodetector are mounted side-by-side on the cuff housing, and blood pressure and oxygen saturation are measured based on reflection of light by tissue in the body member.

Figure 2:
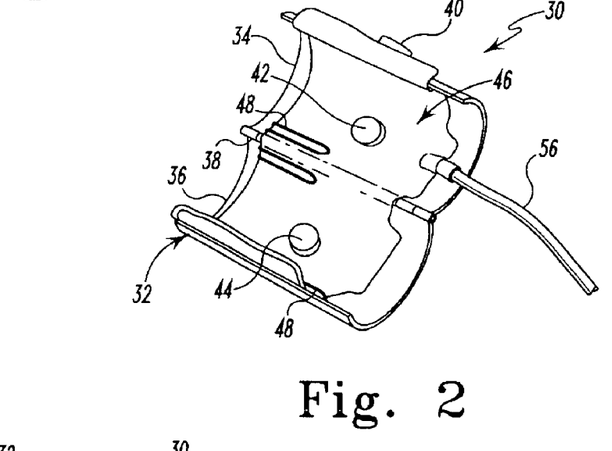
FIG. 2 is a perspective view of a hinged embodiment of a transilluminating pressure cuff according to the present invention.
Figure 3:
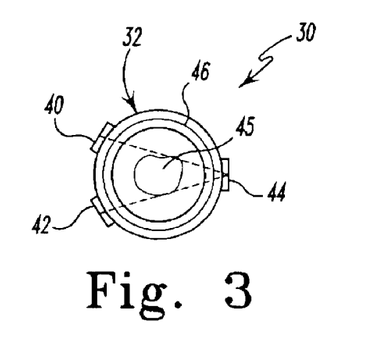
FIG. 3 is a transverse cross-section of the cuff of FIG. 2.

Referring to FIGS. 2 and 3, another embodiment of a cuff 30 according to the present invention includes a hinged cuff housing 32 having first and second semicylindrical sections 34 and 36 and a hinge 38 parallel to the longitudinal axis of the semicylindrical housing sections. The axes of the two housing sections are parallel to each other and coincide to form a common axis when the hinged housing is closed. In order to facilitate use of the cuff on a bone-containing body member, i.e., to avoid bone shadow, two light sources 40 and 42 are circumferentially spaced on one housing section in opposition to a photodetector 44 mounted on the other housing section. This configuration increases the transmission of light through the tissue bed around the bone 45 in the member in which blood pressure is measured noninvasively. The angular spacing of the LEDs and the photodetector may be as shown in FIG. 3, or, alternatively, the LEDs and photodetector may be spaced approximately 120° apart. LEDs such as type L660/805/975-40D00, available from Epitex, Kyoto, Japan, are suitable light sources, and a suitable photodetector is a type QSD723 photoresistor or photodiode available from QT Optoelectronics. The above-referenced LEDs are multi-wavelength LEDs which facilitate the measurement of blood oxygen saturation, as will be described. Alternatively, two monochromatic LEDs may be employed.

An optically transparent, inflatable cuff 46, which may be provided as a disposable item with an inflation tube 56, is adapted to fit within cuff housing 32 and around the body member, and is held in place by means of a plurality of clips 48 which are provided in the housing for this purpose. Single-tube inflation cuffs of the type available from W. A. Baum Company for neonatal applications would be suitable for such purposes if made of material that is transparent to the wavelengths of light emitted by the LEDs. PVC is presently preferred, although latex and polyurethane are also suitable to varying degrees. A similar disposable cuff may also serve as sleeve 14 in the embodiment of FIG. 1. Talcum powder is preferably used with the annular cuff to make it easier to apply and remove the cuff and to help it seat evenly.

The cuff housing may be made of metal or plastic in two separately formed sections connected together by a separate hinge as described above. Alternatively, the semicylindrical sections and the hinge may be formed together as a one-piece plastic housing. In the latter case the housing is substantially thinner at the integral hinge than elsewhere, and in all cases the housing is of suitable thickness to withstand the pressure in the cuff. The housing may be held closed with tape, or a latch, or other suitable means. A suitable axial length for the cuff housing for most human applications is approximately 40% of the circumference of the member for which it is designed to be used. The length of the cuff is preferably determined such that the maximum amplitude of optical oscillations coincides with true mean arterial pressure. If the cuff is too short, it may give a falsely high indirect mean pressure, as identified by the cuff pressure for maximum amplitude optical oscillations. A percentage closer to 45% may be appropriate for small body members. For example, experiments to date indicate that a percentage of 43% is appropriate for a human little finger and for a piglet tail, and a percentage of 45% is appropriate for a rat tail.

Figure 4:
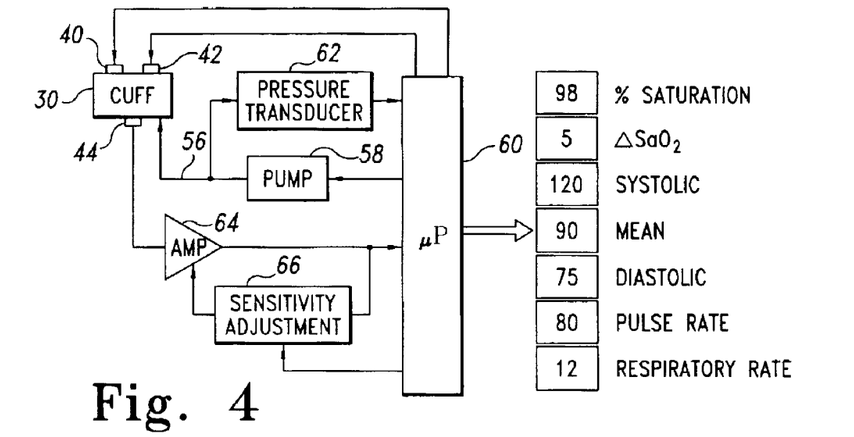
FIG. 4 is a block diagram of a blood parameter measurement system incorporating a member-transilluminating cuff.

Referring to FIG. 4, the cuff is connected by inflation tube 56 to a pump 58 which is controlled by a microprocessor 60. Pressure in the line to the cuff is measured by means of a pressure transducer 62 having a signal output connected to the microprocessor. Suitable transducers are available from Cobe Labs, Littleton, Colo. In embodiments such as that of FIG. 1 in which the cuff has an inlet and an outlet, the pressure transducer is connected to the outlet. A/D conversion may be provided in the microprocessor or in the transducer or with a second A/D converter provided between the two. The microprocessor controls the LEDs and, during blood pressure measurement, energizes both LEDs continually. The photodetector produces an output signal which is supplied to the microprocessor through an amplifier 64. The amplified photodetector output signal is converted to digital form in the microprocessor itself if the microprocessor has an internal A/D converter, or in a separate AID converter provided between the amplifier and the microprocessor.

The microprocessor is suitably programmed to identify, based on the digitized output signal of the photodetector, the points in the cuff pressure signal which correspond to systolic, mean and diastolic pressure, and displays the corresponding values on a display 65 which may comprise separate indicators as shown in FIG. 4, or may provide an output for distant recording.

One suitable embodiment of amplifier 64 is a variable-gain amplifier. With such an amplifier, and with a feedback circuit 66 connected to its gain-control input, as shown in FIG. 4, the sensitivity of the measuring system may be adjusted automatically to a proper level for measurement of blood pressure. It has been found useful to set the sensitivity based on the amplitude of the photodetector output pulses before inflation of the cuff. Such pulses may have a peak-to-peak amplitude on the order of one-third to one-half the maximum peak-to-peak amplitude of the pulses obtained during blood pressure measurement. Such pulses are identified by the reference numeral 68 in FIG. 5, which shows a sample waveform for the photodetector output signal both prior to and during blood pressure measurement. Sensitivity adjustment is inhibited when blood pressure is measured. That is, the gain of amplifier 64 and thus the system sensitivity is fixed at that time. It should be noted that pulse rate can be determined from the optical pulses occurring before cuff inflation and after cuff deflation and may be displayed along with blood pressure values as indicated in FIG. 4.

Figure 5:
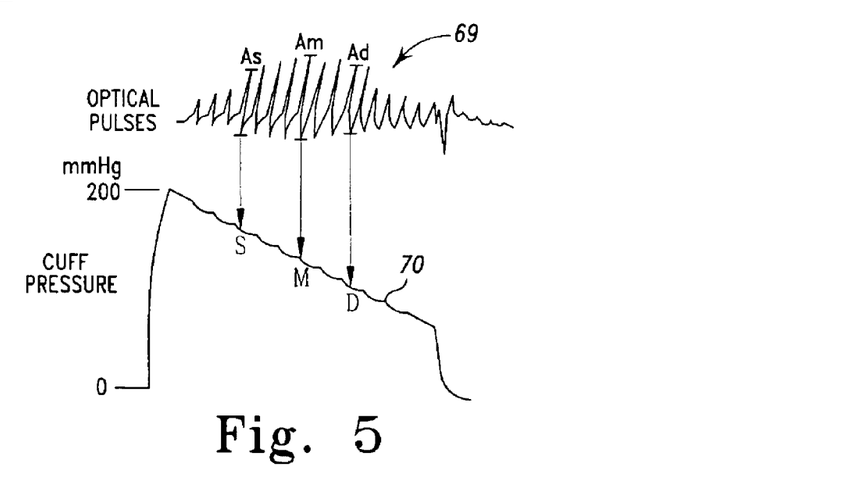
FIG. 5 is a set of sample waveforms obtained from a human subject with a cuff on the little finger according to the present invention.

When cuff pressure is raised above systolic pressure, all oscillations cease. As cuff pressure falls below systolic pressure, the pulses reappear, and as cuff pressure is reduced further, the optical pulse amplitude increases and reaches a maximum, at which point the cuff pressure is believed to equal mean arterial pressure. With a continued decrease in cuff pressure, the oscillation amplitude decreases and returns to a uniform level. FIG. 5 identifies the signals for identifying the points on the cuff pressure curve 70 corresponding to systolic (S), mean (M), and diastolic (D) pressure. FIG. 5 shows a sample optical pulse waveform 69 obtained during a cuff pressure cycle represented by curve 70, and indicates the peak-to-peak amplitudes $A_s$, $A_m$ and $A_d$ of the pulse waveform at the points coinciding respectively with the occurrence of systolic, mean and diastolic pressure. Systolic pressure is identified on the basis of the ratio $A_s/A_m$, and diastolic pressure is identified on the basis of the ratio $A_d/A_m$. Specifically, these fractions are multiplied by the amplitude $A_m$ to obtain the amplitudes $A_s$ and $A_d$, and the corresponding points in time are identified on the optical pulse waveform, by interpolation if necessary between adjacent pulses. Appropriate ratios have been determined experimentally. With a conventional cuff applied to the upper arm of a human subject, and with the cuff width (axial length) equal to 40% of the member circumference, systolic pressure occurs when the amplitude ratio $A_s/A_m$ is 0.50; diastolic pressure occurs with a ratio of $A_d/A_m$ equal to 0.80. The axial length of the cuff is suitably equal to 43–45% of the member circumference for a human little finger and for a rat or piglet tail, as indicated above. Experiments to date indicate that, with a properly sized cuff on a rat tail, the corresponding ratios $A_s/A_m$ and $A_d/A_m$ are 0.6 and 0.85, respectively. For a human little finger, the corresponding ratios $A_s/A_m$ and $A_d/A_m$ are 0.2 and 0.65, respectively.

Figure 6:
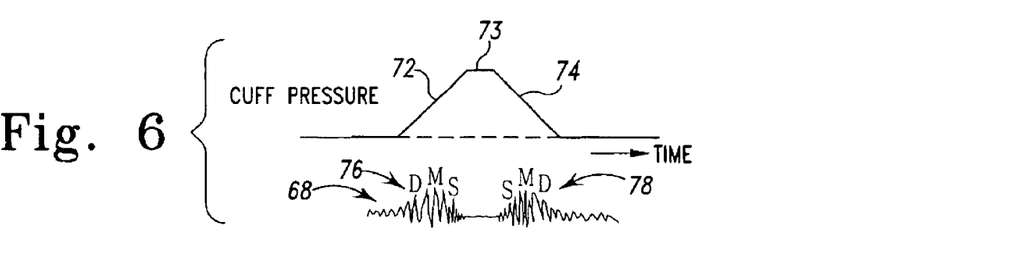
FIG. 6 is another set of sample waveforms.

FIG. 6 illustrates sample waveforms for an embodiment of the invention in which cuff pressure is increased linearly and then decreased linearly, as illustrated respectively by segments 72 and 74 of the cuff pressure signal, and two sets of optical pulsatile data 76 and 78 are acquired. As shown in the drawings, the first set of pulses 76 includes indications of the points in time during the cuff pressure rise 72 at which diastolic, mean and systolic pressure occur, in that order. Conversely, the second set of pulses 78 includes indications of the points in time during the cuff pressure fall 74 at which systolic, mean and diastolic pressure occur, in that order. In this way, two values for each pressure may be acquired and averaged and the average value may be displayed.

Figure 7:
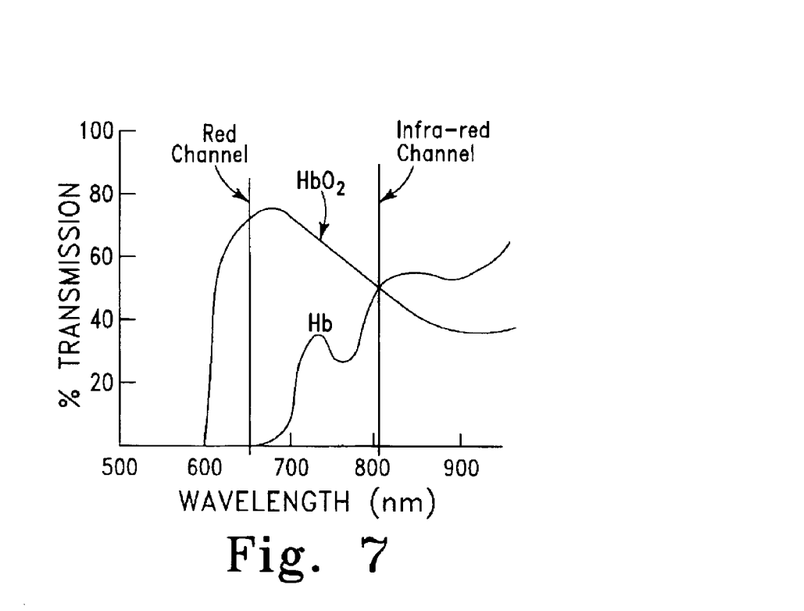
FIG. 7 illustrates the spectral characteristics of hemoglobin (Hb) and oxygenated hemoglobin ($HbO_2$).

Referring again to FIG. 4, the system may include a pulse oximeter for oxygen saturation measurement. Blood oxygen saturation is defined as the ratio of oxygenated hemoglobin ($HbO_2$) to the total hemoglobin ($Hb+HbO_2$), and is typically expressed as a percentage. The pulse oximeter determines oxygen saturation by measuring the optical transmission at two wavelengths of light passing through a tissue bed, such as a fingertip. As shown in FIG. 7, hemoglobin (Hb) has negligible transmission at 650 nm, and hemoglobin (Hb) and oxygenated hemoglobin ($HbO_2$) transmit equally well at 805 nm; the latter wavelength is known as the isobestic point. As can be appreciated from FIG. 7, the transmission at 805 nm is independent of oxygen saturation. Although other wavelengths are contemplated, in the disclosed embodiment, one LED is a red-emitting LED, preferably operating at a wavelength of approximately 650 nm, and the other is an infrared-emitting LED, preferably operating at a wavelength of 805 nm.

The two LEDs are energized alternately in rapid succession, e.g., at a rate of 200 pulses per second. This technique permits the use of high-intensity short-duration pulses. This function may be performed with separate narrowband LEDs, or with one multi-wavelength LED such as the Epitex L660/805/975-40D00 indicated above. In the latter case, one such LED suffices for oximetry. The photodetector may be a broadband detector, such as that identified above, that detects the light transmitted through the member from the red-emitting LED when that LED is energized and then detects the infrared radiation through the member when the infrared LED is energized. Synchronous detection is used to achieve the highest signal-to-noise ratio. Two benefits result: 1) a low average power and minimum heating, and 2) the system is less sensitive to stray ambient illumination. The red and infrared signals are sampled and processed to obtain $SaO_2$. A short display response time and analog and digital outputs may be provided for connection to auxiliary equipment. The automatic sensitivity adjustment is disabled during measurement of oxygen saturation.

A base line for measurement may be established by first inflating the cuff to a high pressure sufficient to squeeze all of the blood out of the member in the cuff and thus out of the optical path. For example, the cuff pressure may be held at a maximum pressure as indicated by the plateau 73 in FIG. 6 for a desired time period to obtain the bloodless transmission reading, which can be assigned a value of 100% transmission. When the cuff pressure is released, blood enters the optical path and the red and infrared transmissions are measured. The optical density is computed for each of the transmitted signals, and the ratio of red to infrared optical density is calculated and scaled to provide an output value corresponding to the percentage of oxygen saturation.

Figure 8:
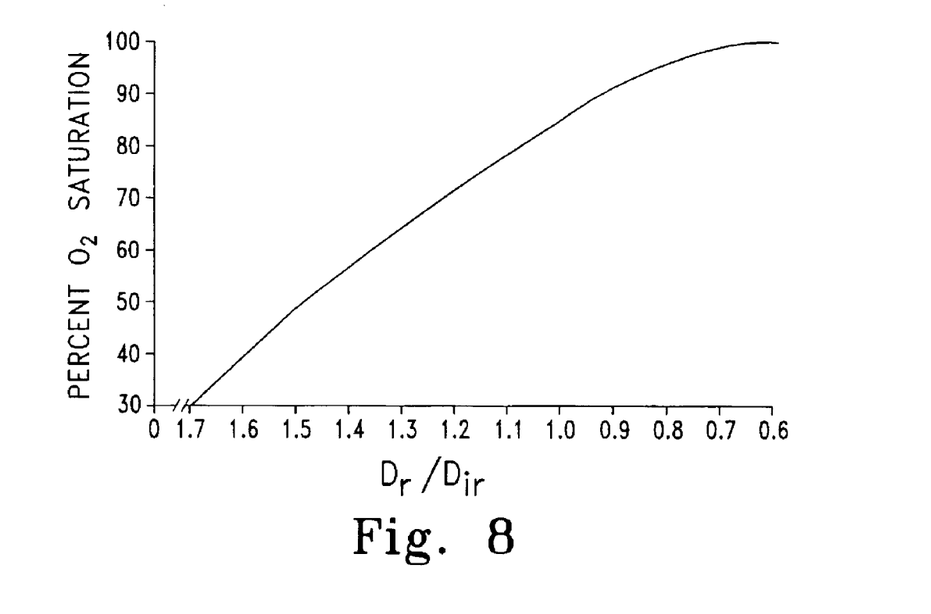
FIG. 8 is an example of a calibration curve for use in oxygen saturation measurement according to the present invention.

Beer's law relates the optical density (D) to the concentration of a dissolved substance. Optical density (D) is equal to log I/T, where T is the transmittance. Therefore the oxygen saturation ($SaO_2$) is given by:

$$SaO_2 = \frac{D_{650}}{D_{805}} + B$$

where B is a constant. This equation predicts a linear relationship based on Beer's law. However, Beer's law applies to solutions in which the absorbing substance is dissolved. Blood is a suspension, and, consequently, the relationship between $SaO_2$ and the ratio of the optical density for red and infrared radiation is nonlinear, as shown in FIG. 8. Between 30% and 60% saturation, the relationship is almost linear; above this range the relationship is nonlinear. The curve in FIG. 8 is an example of a suitable calibration curve which may be programmed into the microprocessor, e.g., in the form of a lookup table, for calculation of $SaO_2$. Further information regarding methods of measuring blood oxygen saturation may be found in the following references which are hereby incorporated by reference: Geddes, "Heritage of the Tissue-Bed Oximeter," *IEEE Engineering in Medicine and Biology*, 87–91, March/April 1997; Geddes and Baker, *Principles of Applied Biomedical Instrumentation*, $3^{rd}$ ed., Wiley, New York, 1989.

Calibration of the oximeter also involves balancing the outputs for the red and infrared channels to obtain the same optical sensitivity for both, and ensuring that both channels have a linear response to the red and infrared radiation.

Figure 9:
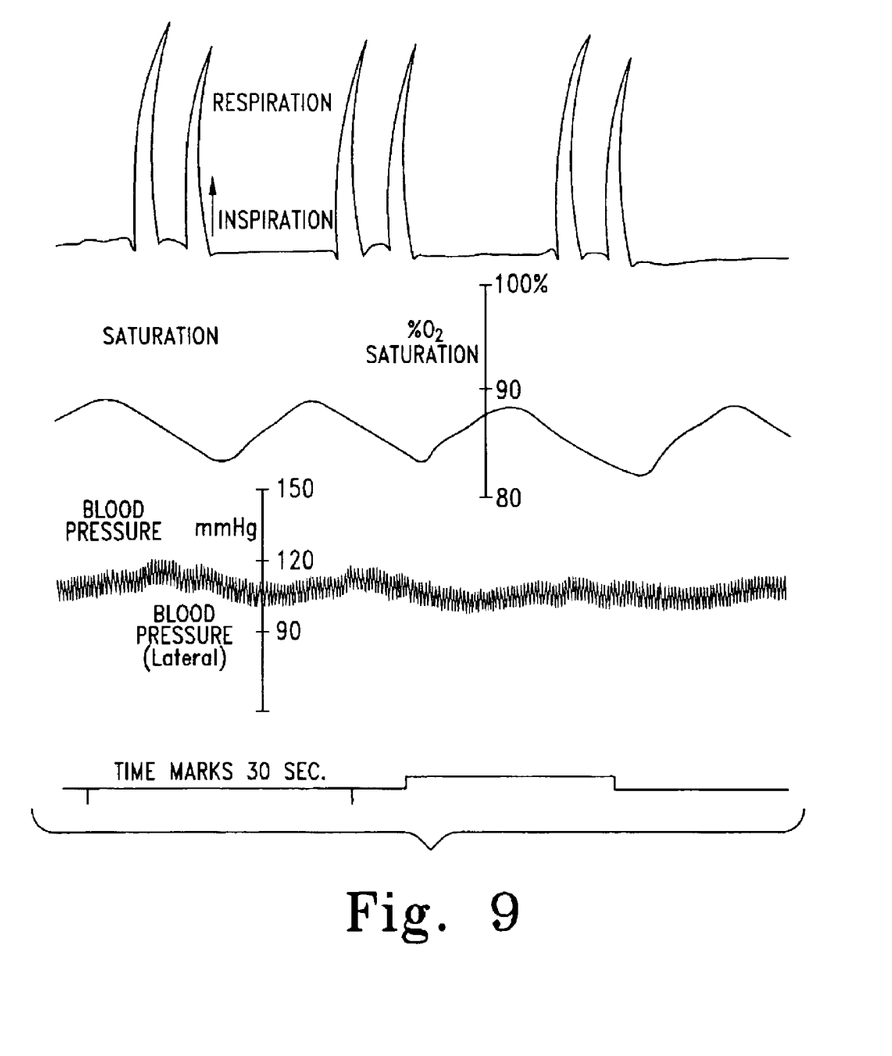
FIG. 9 is a record of respiration, oxygen saturation and blood pressure obtained from an anesthetized dog using a flow-through oximeter.

The present invention also takes advantage of the fact that oxygen saturation varies with breathing. When respiration is slow and deep, oxygen saturation varies considerably, as shown by FIG. 9, a record of respiration, oxygen saturation and blood pressure obtained from an anesthetized dog using a flow-through oximeter. Rhythmic changes in saturation occurring at the respiratory rate may be observed in the graph. Commercially available pulse oximeters have too long a response time to show this important clinical sign of inadequate respiratory rate. The pulse oximeter according to the present invention has a response time short enough to enable it to display this variation in oxygen saturation, which can be used as an indicator in setting a ventilator.

Figure 10:
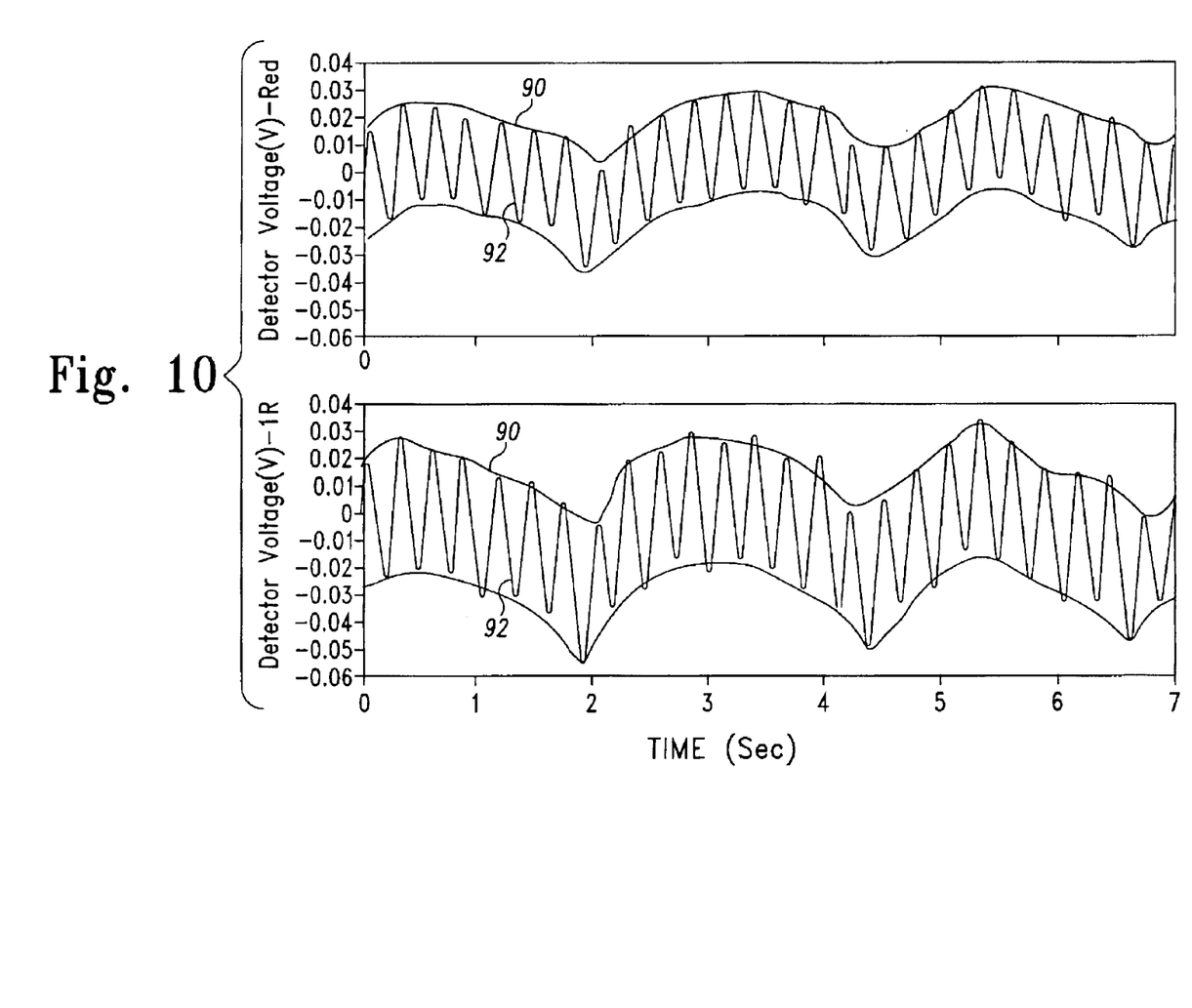
FIG. 10 illustrates respiratory variations in optical transmission through a body member with a cuff according to the present invention.

FIG. 10 shows analog recordings of the transmittance for the red and infrared channels with an annular cuff as described above applied to a piglet tail. The respiratory variations are apparent in the envelope 90 of the pulsatile signal at both wavelengths, and can be separated from the relatively high-frequency oscillations 92 by means of conventional signal processing techniques in order to derive and display respiratory rate.

Figure 11:
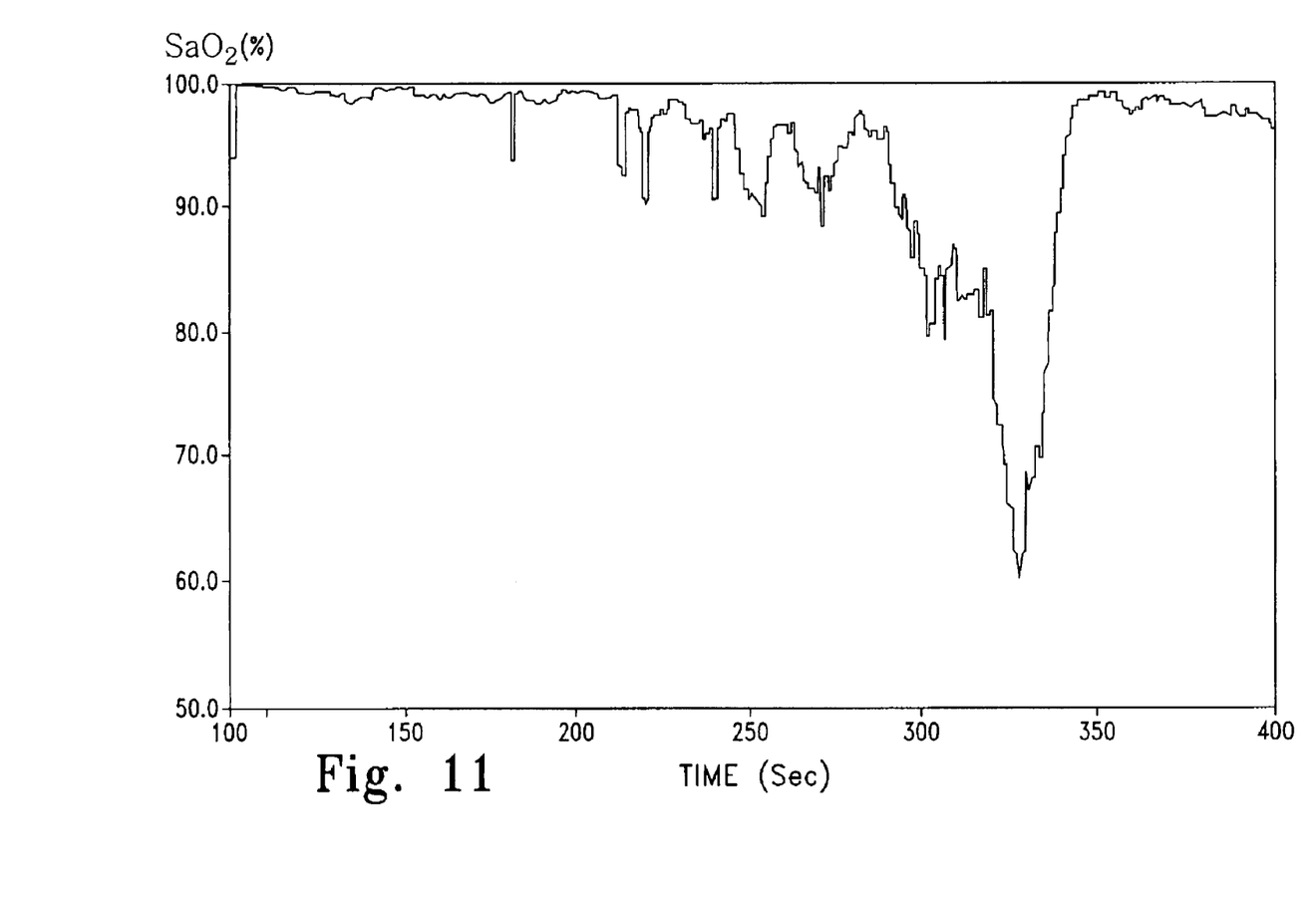
FIG. 11 is a record of oxygen saturation as a function of time during breath holding in a human subject.

FIG. 11 is a record of oxygen saturation versus time for a human subject. The $SaO_2$ displayed is a moving five-heartbeat average. On the left the subject is breathing normally and the blood is about 99% saturated. However, the signal contains small variations due to respiration. The larger ensuing variations in $SaO_2$ occurred when the subject hyperventilated; then the subject held his breath for 1½ minutes and the $SaO_2$ decreased to about 60%, at which time the subject inhaled deeply and experienced an extremely rapid rise in $SaO_2$.

It will be appreciated from the above that the disclosed system provides significant advantages over prior art devices by providing pulse recording, blood pressure measurement and oxygen saturation measurement with a single transducer. Further, it will be appreciated that when the cuff is inflated, it provides automatic centering of the member in the cuff and thereby assures proper alignment.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, although the embodiment of FIG. 2 is described above as having two emitters and one detector, it may instead be provided with one emitter and two detectors or with a combination of multiple emitters and multiple detectors. The system may also be provided with an alarm which is triggered when the transducer is off the body member desired to be monitored; an alarm circuit may be designed to respond, for example, to an optical sensor output signal level that is beyond a predetermined threshold, indicative of the absence of absorbing material in the optical path, or to such a condition combined with the additional condition of an absence of optical pulses.

We claim:

1. A member-transilluminating cuff for optical noninvasive measurement of blood parameters, comprising:
    a hinged cuff housing having first and second semicylindrical sections and a hinge parallel to the longitudinal axes of said semicylindrical housing sections;
    a light source mounted on said first housing section;
    a photodetector mounted on said second housing section in a position to receive light transmitted from said light source through a body member placed within said cuff housing; and
    a transmissive, inflatable cuff adapted to fit within said cuff housing and around said body member.

2. A The member-transilluminating cuff of claim 1, wherein said cuff housing is a one-piece housing including said hinge.

3. The member-transilluminating cuff of claim 1, further comprising a second light source mounted on said first housing section, said light sources being spaced apart circumferentially.

4. A member-transilluminating cuff for optical noninvasive measurement of blood parameters, comprising:
    a hinged cuff housing having first and second semicylindrical sections and a hinge parallel to the longitudinal axes of said semicylindrical housing sections;
    a light source mounted on said first housing section;
    a photodetector mounted on said second housing section in a position to receive light transmitted from said light source through a body member placed within said cuff housing; and
    an inflatable cuff adapted to fit within said cuff housing and around said body member,
    wherein said inflatable cuff is a readily replaceable cuff.

5. A member-transilluminating blood parameter measurement system, comprising:
    a transilluminating cuff for encircling a body member, said cuff including a light source and a light detector and having a transmissive, inflatable portion with a surface thereof separating said light source and light detector from said body member;
    optical oscillometric circuit means connected to said transilluminating cuff for measuring blood pressure; and
    means connected to said transilluminating cuff for measuring blood oxygen saturation.

6. The system of claim 5, further comprising means connected to said transilluminating cuff for measuring pulse rate.

7. The system of claim 6, wherein said cuff is a clamshell cuff.

8. The system of claim 6, wherein said cuff is an annular cuff.

9. The system of claim 5, wherein said optical oscillometric circuit means includes means for measuring blood pressure during consecutive upward and downward transitions in cuff pressure and calculating an average of blood pressure values obtained during said consecutive transitions.

10. The system of claim 5, wherein said circuit means for determining blood oxygen saturation includes means for obtaining a substantially bloodless transmission reading, corresponding to substantially 100% transmission, at a point at which cuff pressure is greater than normal systolic pressure.

11. A member-transilluminating cuff for optical noninvasive measurement of blood parameters, comprising:
    a cuff housing;
    a light source mounted in said housing;
    a photodetector mounted in said housing in a position to receive light transmitted from said light source through a body member placed within said cuff housing; and
    an inflatable cuff readily removably mounted in said housing between said light source and said photodetector in a position to receive light generated by said light source, wherein said inflatable cuff is at least partially transmissive at a wavelength of light generated by said light source.

12. An optical noninvasive system for the measurement of blood parameters in infant limbs, comprising:
    a cuff housing sized to fit an infant limb;
    a transmissive, inflatable cuff mounted in said housing;
    an optical sensor including a light source and detector mounted in said housing; and optical oscillometric circuit means responsive to an output signal from said optical sensor for determining systolic pressure, mean pressure and diastolic pressure during a transition in cuff pressure between a pressure greater than normal systolic pressure and a pressure less than normal diastolic pressure.

13. The system of claim 12, further comprising circuit means responsive to an output signal from said optical sensor for determining pulse rate.

14. The system of claim 13, further comprising circuit means responsive to an output signal from said optical sensor for determining respiratory rate.

15. The system of claim 14, further comprising circuit means responsive to an output signal from said optical sensor for determining blood oxygen saturation, wherein said light source includes first and second narrowband LEDs emitting at respective wavelengths of approximately 650 nm and approximately 805 nm and optically linked to said detector.

16. The system of claim 15, wherein said circuit means for determining blood oxygen saturation determines oxygen saturation according to a nonlinear relationship between oxygen saturation and the ratio of the optical densities for the radiation from said narrowband LEDs.

17. The system of claim 12, further comprising circuit means responsive to an output signal from said optical sensor for determining respiratory rate.

18. The system of claim 12, further comprising circuit means responsive to an output signal from said optical sensor for determining blood oxygen saturation, wherein said light source includes first and second narrowband LEDs emitting at respective wavelengths of approximately 650 nm and approximately 805 nm and optically linked to said detector.

19. The system of claim 12, wherein said cuff housing has a clamshell shape.

20. The system of claim 12, wherein said cuff housing is an annular housing.

21. The system of claim 12, wherein said optical oscillometric circuit means includes means for measuring blood pressure during consecutive upward and downward transitions in cuff pressure and calculating an average of blood pressure values obtained during said consecutive transitions.

22. The system of claim 12, wherein said circuit means for determining blood oxygen saturation includes means for obtaining a substantially bloodless transmission reading, corresponding to substantially 100% transmission, at a point at which cuff pressure is greater than normal systolic pressure.

23. A member-transilluminating cuff for optical noninvasive measurement of blood parameters, comprising:

a cuff housing;

a light source mounted in said housing;

a photodetector mounted in said housing in a position to receive light transmitted from said light source through a body member placed within said cuff housing; and an inflatable cuff readily removably mounted in said housing and positioned therein at least partially in the path of light from said light source to said photodetector, wherein said inflatable cuff is at least partially transmissive at a wavelength of light generated by said light source.

* * * * *

UNITED STATES PATENT AND TRADEMARK OFFICE
CERTIFICATE OF CORRECTION

PATENT NO. : 6,801,798 B2
DATED : October 5, 2004
INVENTOR(S) : Geddes et al.

It is certified that error appears in the above-identified patent and that said Letters Patent is hereby corrected as shown below:

Title page,
Item [56], References Cited, OTHER PUBLICATIONS, "Patrick G. Yong, Bsee, and Leslie G. Geddes, ME, PhD, FACC," reference, please change "Bsee" to -- BSEE --

Column 1,
Line 26, please change "pulsatilc" to -- pulsatile --

Column 4
Line 36, please change "AID" to -- A/D --

Column 6,
Line 32, please change "I/T" to -- l/T --

Column 7,
Line 63, please delete "A"

Signed and Sealed this

Seventeenth Day of May, 2005

JON W. DUDAS
*Director of the United States Patent and Trademark Office*